United States Patent [19]

Berky et al.

[11] 4,247,646
[45] Jan. 27, 1981

[54] LABORATORY APPARATUS FOR CLONING MAMMALIAN CELLS

[75] Inventors: John J. Berky, Little Rock; John Hunziker, Jr., Pine Bluff; Laurence A. Zolotor, Little Rock, all of Ark.

[73] Assignee: The United States of America as represented by the Department of Health, Education and Welfare, Washington, D.C.

[21] Appl. No.: 941,666

[22] Filed: Sep. 12, 1978

[51] Int. Cl.³ .................... C12M 3/00; C12M 1/00
[52] U.S. Cl. .................................. 435/284; 30/301; 30/358; 435/287
[58] Field of Search ............. 435/284, 285, 286, 287, 435/292, 297, 298, 299; 30/301, 358

[56] References Cited

U.S. PATENT DOCUMENTS

| 268,886 | 12/1882 | Hall | 30/301 |
|---|---|---|---|
| 2,140,266 | 12/1938 | Leeberg | 30/301 |
| 2,290,648 | 7/1942 | McCain | 30/301 |
| 2,526,811 | 10/1950 | Dawson | 30/301 |
| 2,871,168 | 1/1959 | Salisbury, Jr. | 195/139 |
| 3,334,809 | 8/1967 | Zajic et al. | 30/358 X |
| 3,482,311 | 12/1969 | Farris | 435/287 |
| 3,791,930 | 2/1974 | Saxholm | 195/103.5 R |
| 3,985,608 | 10/1976 | Saxholm | 195/127 |
| 4,053,362 | 10/1977 | Sforza | 195/103.5 R |
| 4,072,578 | 2/1978 | Cady et al. | 195/127 |

Primary Examiner—Robert J. Warden
Attorney, Agent, or Firm—John S. Roberts, Jr.

[57] ABSTRACT

Laboratory apparatus for cloning mammalian cells includes a support plate and a plurality of tubular cylinders fixedly secured within the plate and projecting from one face thereof. All of the cylinders, with the exception of one pair, are disposed within a concentrated array defined within a predetermined sector region of the plate, the remaining pair of cylinders being located remote from the sector array yet equidistantly spaced from each other and from the sector array so as to complete the distribution pattern. A substantially C-shaped ring member is fixedly secured to, or integrally formed with, the opposite face of the support plate, in order to facilitate maneuverability of the assemblage when placing the same onto a Petri dish for isolating the colonies developing thereon. The plate and ring member are fabricated from transparent polycarbonate in order to permit the colonies to be identified or viewed by background lighting techniques. The distal ends of the isolating cylinders are also sharply beveled in order to cut into or penetrate the Petri dish so as to sealingly isolate the colonies.

13 Claims, 13 Drawing Figures

LABORATORY APPARATUS FOR CLONING MAMMALIAN CELLS

FIELD OF THE INVENTION

The present invention relates generally to laboratory apparatus, and more particularly to laboratory apparatus which will efficiently faciliate the cloning of mammalian cells.

BACKGROUND OF THE INVENTION

While laboratory apparatus exists for the promotion of growth of bacterial colonies, or other similar colonies of cultures, such apparatus is not adaptable for the cloning of mammalian cells due to the differences in the growth characteristics of such colonies. Bacterial colonies, for example, develop of grow upon the surface of the nutritional substrate disposed within a Petri dish, while mammalian cells develop or grow upon the bottom surface of the Petri dish. In accordance with conventional laboratory techniques, particular colonies are to be isolated, both in the growth or development of bacterial cultures and mammalian cultures, however, due to the aforenoted differences in the growth characteristics of such colonies, the means employed within the laboratory apparatus for isolating the colonies are necessarily different. Consequently, the apparatus employed for isolating and promoting the development of bacterial cultures cannot be utilized for isolating and developing mammalian cultures.

The means employed within conventional laboratory apparatus for isolating the culture colonies usually takes the form of specifically configured or structured grids, tubular cylinders, and the like, operatively associated with the Petri dishes. Laboratory experience has also demonstrated the fact that the aforenoted bacterial and mammalian colonies develop upon the nutritive material and the Petri dish surface, respectively, in predetermined arrays or patterns. Bacterial colonies, for example, tend to develop upon all regions of the nutritive material while mammalian cultures tend to develop only upon a predetermined region or sector of the Petri dish. Consequently, in order to efficiently promote the development of the mammalian colonies, the laboratory apparatus must comprise specifically arranged isolated means. Conventionally arranged isolation devices cannot in fact be employed due to the fact that such means would not properly isolate the colonies. The grid concentration, for example, is insufficient within the development sector, and is excessive and unnecessary within the remaining portions of the apparatus.

OBJECTS OF THE INVENTION

Accordingly, it is an object of the present invention to provide new and improved laboratory apparatus.

Another object of the present invention is to provide new and improved laboratory apparatus which is particularly suitable for cloning mammalian cells.

Still another object of the present invention is to provide new and improved laboratory apparatus which is particularly adapted for promoting the cloning of mammalian cell colonies by properly implementing the isolation of the colonies.

Yet another object of the present invention is to provide new and improved laboratory apparatus which is relatively simplistic in structure and relatively inexpensive to manufacture.

SUMMARY OF THE INVENTION

The foregoing and other objectives are achieved in accordance with the present invention through the provision of laboratory apparatus for cloning mammalian cell colonies which includes an assemblage comprising a transparent plate or disc, and a multitude of tubular cylinders fixedly secured within the plate and projecting from one face thereof. All of the cylinders, with the exception of one pair, are disposed within a concentrated array defined within a predetermined sector region of the plate, the remaining pair of cylinders being spaced substantially equidistantly from each other and the primary cylinder array. With the foregoing arrangement of the clone colony isolation cylinders, all possible combinations, and areas, with respect to a particular "sweep" over the associated Petri dish and the developing colonies, will be encompassed by the apparatus. In addition, the remote pair of circumferentially spaced cylinders also impart stability to the assemblage when the same is mated with the Petri dish.

The assemblage also includes a substantially C-shaped ring member fixedly secured to, or integrally formed with, the face of the plate opposite that face from which the cylinders protrude. The C-shaped ring member serves to define means whereby the entire assemblage may be easily held or grasped, and the maneuverability of the same facilitated, when the apparatus is to be mated with the Petri dish upon which the mammalian colonies are developing. Both the plate and the ring member are fabricated from transparent polycarbonate, and in this manner, the assemblage may be accurately positioned relative to the developing colonies, whereby the same may be isolated by means of the tubular cylinders, in accordance with background lighting techniques. In order to in fact isolate the colonies when the assemblage is mated with the Petri dish, the distal ends of the tubular cylinders are beveled such that the same may cut into or pierce the upper surface of the Petri dish thereby forming seals therewith.

BRIEF DESCRIPTION OF THE DRAWINGS

Various other objects, features, and attendant advantages of the present invention will be more fully appreciated as the same becomes better understood from the following detailed description when considered in conjunction with the accompanying drawings, in which like reference characters designate like or corresponding parts throughout the several views, and wherein.

DETAILED DESCRIPTION OF THE ILLUSTRATED EMBODIMENT

Figure 1:
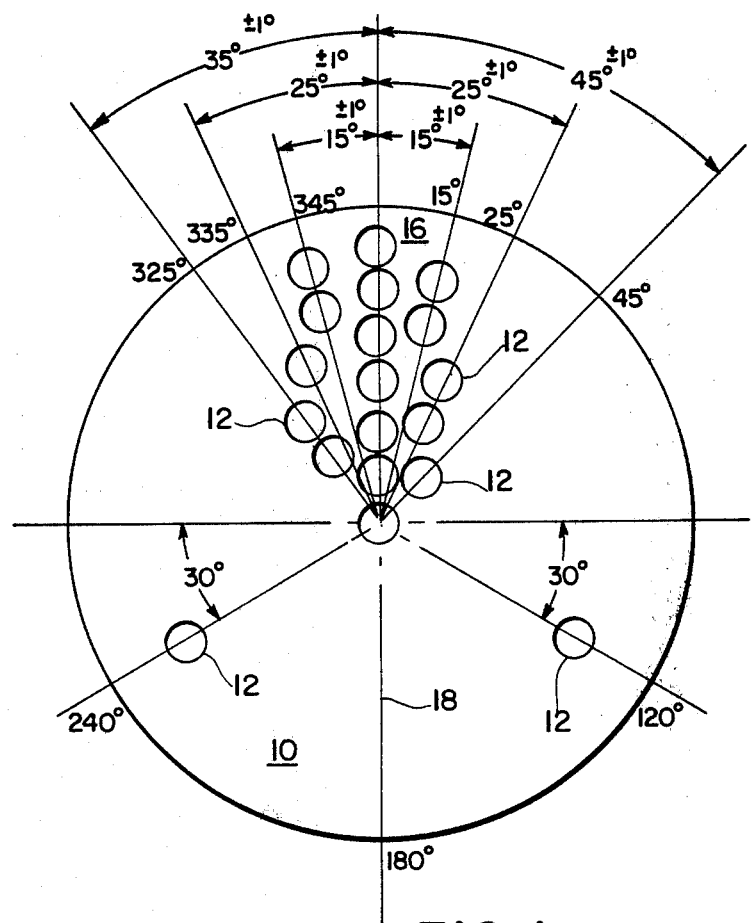
FIG. 1 is a plan view of the support plate of the laboratory apparatus of the present invention, showing the arrangement of the holes or apertures within which the cloning colony isolation cylinders are to be fixedly secured.
Figure 5:
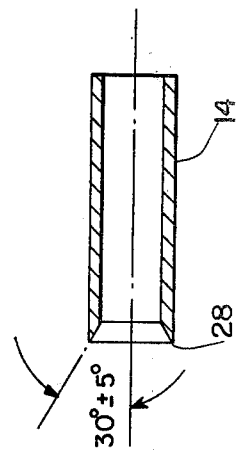
FIG. 5 is a cross-sectional view of one of the tubular cylinders of the present invention showing its beveled distal end adapted to cut into or penetrate the surface of the Petri dish in order to accomplish the required seal for clone isolation.

Referring now to the drawings, and more particularly to FIGS. 1 and 5 thereof, the laboratory apparatus of the present invention is seen to comprise a circular support plate or disc 10 which may have a thickness of approximately one-quarter inch ($\frac{1}{4}''$) and a diameter of 2.062 inches so as to be capable of operatively mating with a standard 60 mm Petri dish. Of course larger support plates may be utilized if, for example, 100 mm Petri dishes are being employed.

Figure 4:
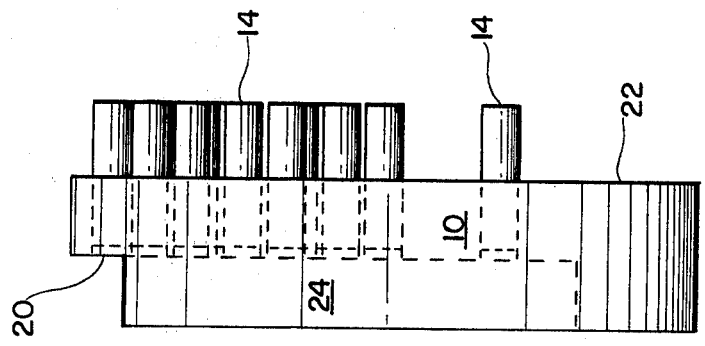
FIG. 4 is a side elevation view of the assemblage of FIG. 3.
Figure 3:
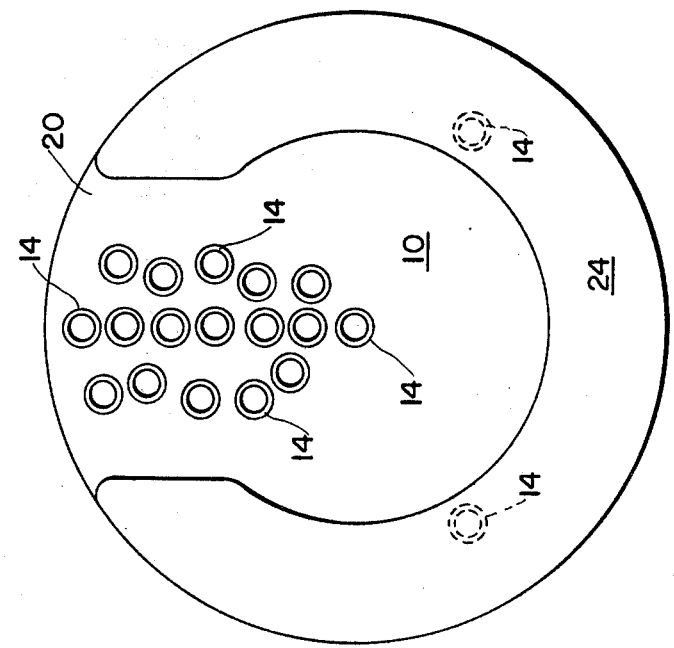
FIG. 3 is a plan view of the support plate-holding ring assemblage of the present invention as the same would appear when disposed over a Petri dish for clone isolation purposes.

As particularly seen from FIG. 1, plate 10 is provided with a plurality of through-bores 12, such as, for example, nineteen, and as seen from FIGS. 3 and 4, tubular cylinders 14, as particularly shown in FIG. 5, are adapted to be disposed within the bores. The bores 12 defined within plate 10 are disposed within a predetermined pattern or array so as to define a particular distribution arrangement for the tubular cylinders 14 whereby the latter may be disposed within a majority of the areas normally occupied by the mammalian cell colonies developing upon the bottom of a Petri dish, not shown. Such a distribution pattern accounts for all possible combinations and areas within a particular "sweep" over the surface of the Petri dish, and in this manner, as will become more apparent hereinafter, the tubular cylinders 14 may be optimally located so as to perform their clone colony isolation functions.

With continued reference to FIG. 1, it is seen that the bores 12 are defined along particularly oriented radii of plate 10, and that the vast majority of the bores 12, and the cylinders 14 to be fixedly secured therein, are concentrated within a predetermined sector of plate 10, the sector being generally indicated by the reference character 16. If a vertical plane 18, as viewed in FIG. 1, was designated as the 0°–180° plane, then it is seen that in accordance with the present invention, the sector 16, within which all of the centers of the bores 12 are located, would be bounded by the 45° and 325° radii, and that the arcuate extent of the sector 16 would encompass 80°.

As noted hereinbefore, the bores 12 are defined along predetermined radii and are arranged in sets. The first set of bores comprises seven bores and the centers of the bores are all located along the plane 18 and extend from the center of plate 10 radially outwardly. The bores 12 are approximately 0.134 inches in diameter, ±0.002 inches, and the centers of the bores are spaced 0.150 inches from each other along the radii, ±0.005 inches.

A second set of bores is arranged along the 15° radius of the plate, with the center of the radially inner bore being defined at 0.650 inches from the center of the plate. A third set of bores, comprising two bores as was the case of the second set of bores, is defined along the 25° radius of the plate with the radially inner bore being having its center located at 0.350 inches from the plate center. A single bore, which may be said to form a set with the bore defined at the plate center, is located along the 45° radius of the plate and has its center located at 0.200 inches from the plate center.

A fifth bore set is defined along the 345° radius of the plate in a manner similar to that of the second set, however, it is noted that the center of the radially inner bore is located 0.700 inches from the plate center. A single bore, having its center located 0.550 inches from the plate center, defines a sixth set of bores along with the bore located at the plate's center, and it is seen that this set of bores has its centers located along the 335° radius. Lastly, a seventh set of bores is defined along the 325° radius of the plate, with the radially inner bore having its center located 0.250 inches from the plate center.

Aside from the aforenoted bore sets located within sector 16, it is also noted that an auxiliary pair of bores are defined within regions of plate 10 remote from sector 16. These bores permit their corresponding cylinders 14 to complete the predetermined distribution pattern, and as will be apparent hereinafter, when the plate-cylinders assemblage is to be mated with the Petri dish, not shown, the auxiliary cylinders also impart considerable stability to the assemblage relative to the Petri dish. The auxiliary bores and cylinders are defined along the 120° and 240° radii of the plate 10, and consequently, are seen to be substantially equidistant from each other as well as from the concentrated array of bores and cylinders within sector 16. The centers of the auxiliary bores and cylinders are located approximately 0.750 inches from the plate center.

Figure 2:
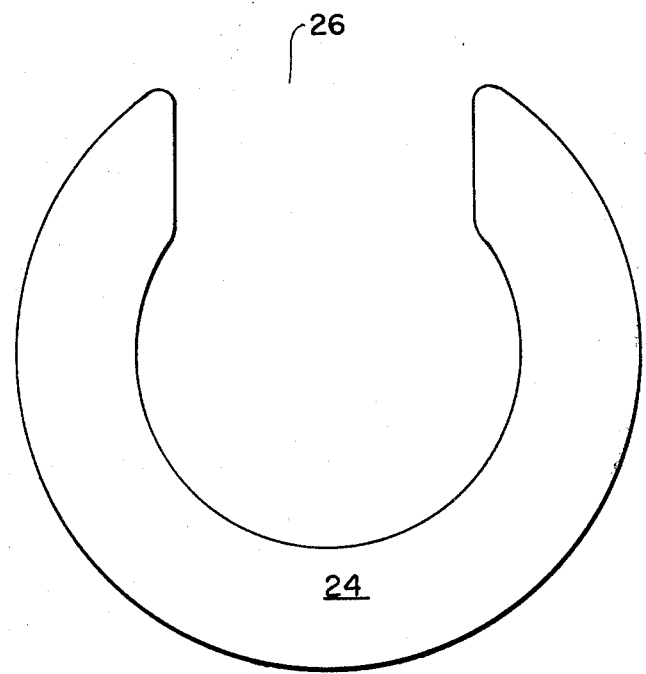
FIG. 2 is a plan view of the holding ring of the apparatus of the present invention.

As may be particularly appreciated from FIG. 4, when the cylinders 14 are fixedly secured within the support plate 10, the proximal ends thereof are coplanar with one surface 20 of the plate, while the distal ends of the cylinders project away from the opposite surface 22 thereof. With additional reference being made to FIGS. 2 and 3, it is seen that the laboratory apparatus of the present invention also comprises a substantially C-shaped holding ring 24 which is adapted to be fixedly secured to the face 20 of plate 10. Ring 24 is similar to plate 10 in that its thickness is approximately one-quarter inches ($\frac{1}{4}''$) and the outside diameter thereof is 2.062 inches. The inside diameter is correspondingly 1.25 inches ±0.010 inches. As may be surmised, the ring member 24 facilitates the holding or grasping of the entire assemblage comprising the present invention as the same is maneuvered for accuately placing the clone colony isolation cylinders 14 relative to the colonies developing upon the bottom surface of the Petri dish, not shown.

In order to in fact assure that the cylinders 14 are disposed properly with respect to particular clone colonies, both the plate 10 and the ring 24 are fabricated from a light transmissive or transparent synthetic thermoplastic resin, such as, for example, polycarbonate. It is also seen that the open region 26 defined between the free ends of ring 24 is substantially symmetrically disposed with respect to the concentrated cylinder sector 16 of plate 10. This conjunctive assembly defined between ring 24 and plate 10 facilitates the placement of the cylinders 14 relative to the clone colonies. In addition, the transparency characteristics of the plate 10 and ring 24 permit particular clone colonies, disposed below the apparatus assemblage, to be viewed by a laboratory technician, whose field of view is disposed above the apparatus assemblage, by means of background light techniques.

With reference again being made to FIGS. 4 and 5, it is seen that the distal ends of the clone isolating cylinders 14 are disposed in a coplanar manner, and that such ends include sharply beveled peripheral edges 28. Typically, such beveled edges may exhibit taper angles of, for example, 30°±5° with respect to the axial plane of the cylinders. The tubes are preferably fabricated of stainless steel and have a thickness of 0.031 inches, ± 0.002 inches. These structural characteristics impart sufficient rigidity to the cylinders such that when the entire assemblage is to be mated with the Petri dish, not shown, upon which the clone colonies are developing, the cylinders are able to cut into or penetrate the surface of the Petri dish so as to isolate the particular clone colonies and seal off such areas of the dish as defined by each cylinder.

In utilizing the laboratory apparatus of the present invention, when particular clone colonies have been viewed or identified upon the Petri dish, and have been designated for isolation, the plate-ring-cylinders assemblage comprising the apparatus of the present invention may then be held above the Petri dish and maneuvered relative to the particular clone colonies in order to accurately align the isolating cylinders 14 with respect to the colonies. The distribution pattern of the cylinders 14 within sector 16 is critical to the present invention in that the same permits the assemblage to be rotated relative to the Petri dish while nevertheless insuring the fact that a particular location of a specific clone colony can be "swept" or encompassed by the cylinders 14 and therefore isolated as desired. As noted hereinbefore, the accurate placement of the assemblage upon the Petri dish is accomplished by background lighting techniques, which is facilitated by the transparency of the plate 10 and ring member 24. When the angular orientation of the assemblage has been achieved relative to the Petri dish, the assemblage is simply pressed downwardly toward or onto the dish such that particular cylinders 14 surround particular colonies to be isolated. The beveled ends 28 of the cylinders will pierce or penetrate the dish whereupon the isolation of the colonies, and sealing of the same, will have been completed.

Obviously, many modifications and variations of the present invention are possible in light of the above teachings. It is therefore to be understood that within the scope of the appended claims, the present invention may be practiced otherwise than as specifically described herein.

What is new and desired to be secured by Letters Patent of the United States is:

1. Laboratory apparatus for cloning mammalian cells developing upon the surface of a Petri dish, comprising:
   a support plate; and
   a plurality of tubular cylinders fixedly secured within said support plate and projecting from one surface thereof so as to be capable of surrounding and isolating particular mammalian cells developing upon a Petri dish, said plurality of tubular cylinders being concentrated within a sector of said support plate so as to define a predetermined distribution pattern with two remote tubular cylinders disposed away from said sector for insuring said isolation of particular mammalian cells.

2. Laboratory apparatus as set forth in claim 1, wherein:
   said support plate is circular as seen in plan view; and
   said sector of said support plate subtends as 80° arcuate extent of said circular plate.

3. Laboratory apparatus as set forth in claim 2, wherein:
   said tubular cylinders are arranged in sets, the centers of said cylinders of each set being disposed along radial lines of said plate.

4. Laboratory apparatus as set forth in claim 1, wherein:
   the distal ends of said cylinders are sharply beveled such that the same are able to pierce said surface of said Petri dish so as to sealingly isolate said cells.

5. Laboratory apparatus as set forth in claim 1, further comprising:
   a pair of auxiliary tubular cylinders, located remote from said plurality of cylinders located within said plate sector and spaced equidistantly from each other and said sector, for supplementing said predetermined distribution pattern.

6. Laboratory apparatus as set forth in claim 1, further comprising:
   means for facilitating the holding or grasping of said support plate-cylinders assemblage.

7. Laboratory apparatus as set forth in claim 6, wherein:
   said means comprises a substantially C-shaped ring member fixedly secured to the surface of said support plate opposite the surface from which said cylinders project.

8. Laboratory apparatus as set forth in claim 7, wherein:
   said C-shaped ring member is oriented so as to be symmetrically located with respect to said cylinders.

9. Laboratory apparatus as set forth in claim 7, wherein:
   said C-shaped ring member is fabricated from a transparent thermoplastic resin.

10. Laboratory apparatus as set forth in claim 9, wherein:
    said resin is polycarbonate.

11. Laboratory apparatus as set forth in claim 1, wherein:
    said support plate is fabricated from a transparent thermoplastic resin.

12. Laboratory apparatus as set forth in claim 11, wherein:
    said resin is polycarbonate.

13. Laboratory apparatus as set forth in claim 1, wherein:
    said cylinders are fabricated from stainless steel.

* * * * *